United States Patent [19]

Williams et al.

[11] Patent Number: 5,737,013

[45] Date of Patent: *Apr. 7, 1998

[54] DENTAL VIDEO CAMERA WITH AN ADJUSTABLE IRIS

[76] Inventors: Ronald R. Williams, 24872 Sea Aire, Dana Point, Calif. 92629; Steve Wright, 2621 Costebelle Dr., La Jola, Calif. 92039; Fred G. Kinley, 21432 La Capilla, Mission Viejo, Calif. 92691

[*] Notice: The term of this patent shall not extend beyond the expiration date of Pat. No. 5,523,782.

[21] Appl. No.: 426,119

[22] Filed: Apr. 20, 1995

Related U.S. Application Data

[63] Continuation-in-part of Ser. No. 303,019, Sep. 8, 1994, Pat. No. 5,523,782, which is a continuation-in-part of Ser. No. 943,716, Sep. 11, 1992.

[51] Int. Cl.$^6$ ........................................ H04N 5/225
[52] U.S. Cl. ........................... 348/66; 348/68; 606/17; 433/29
[58] Field of Search ........................... 348/65, 66, 68, 348/74, 207; 433/28; 606/14, 17

[56] References Cited

U.S. PATENT DOCUMENTS

| | | | |
|---|---|---|---|
| 4,755,873 | 7/1988 | Kobayahsi | 348/65 |
| 4,757,381 | 7/1988 | Cooper et al. | 348/66 |
| 4,765,313 | 8/1988 | Kumakura | 348/65 |
| 4,941,457 | 7/1990 | Hasegawa | 348/65 |
| 5,016,098 | 5/1991 | Cooper et al. | 348/66 |
| 5,523,782 | 6/1996 | Williams | 348/66 |

*Primary Examiner*—Wendy Garber
*Attorney, Agent, or Firm*—W. Edward Johansen

[57] ABSTRACT

A dental video camera includes a housing which has an elongated cavity with a distal end and a proximal end, an adjustably focusing lens and CCD camera system which is disposed within the elongated cavity of the housing, a fixed focusing lens system and an adjustable iris. The adjustably focusing lens and CCD camera system provides a focusing adjustment between a near field of focus and a far field of focus. The fixed focusing lens system is optically coupled to the adjustably focusing lens and CCD camera system and is disposed in the elongated cavity of the housing adjacent to the distal end thereof. The adjustable iris is optically and mechanically coupled to the adjustably focusing lens and CCD camera system. The adjustable iris is adjusted between a nearly closed opening and a wide open opening in response to the focusing adjustment between the near field of focus and the far field of focus.

17 Claims, 9 Drawing Sheets

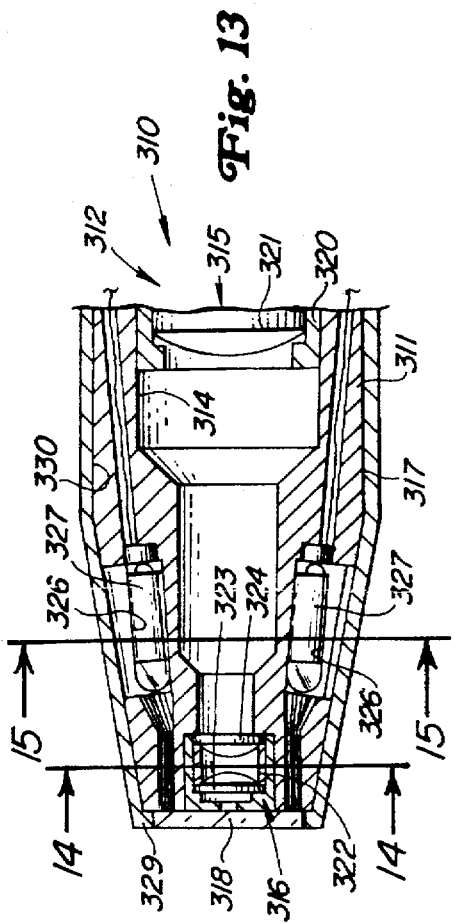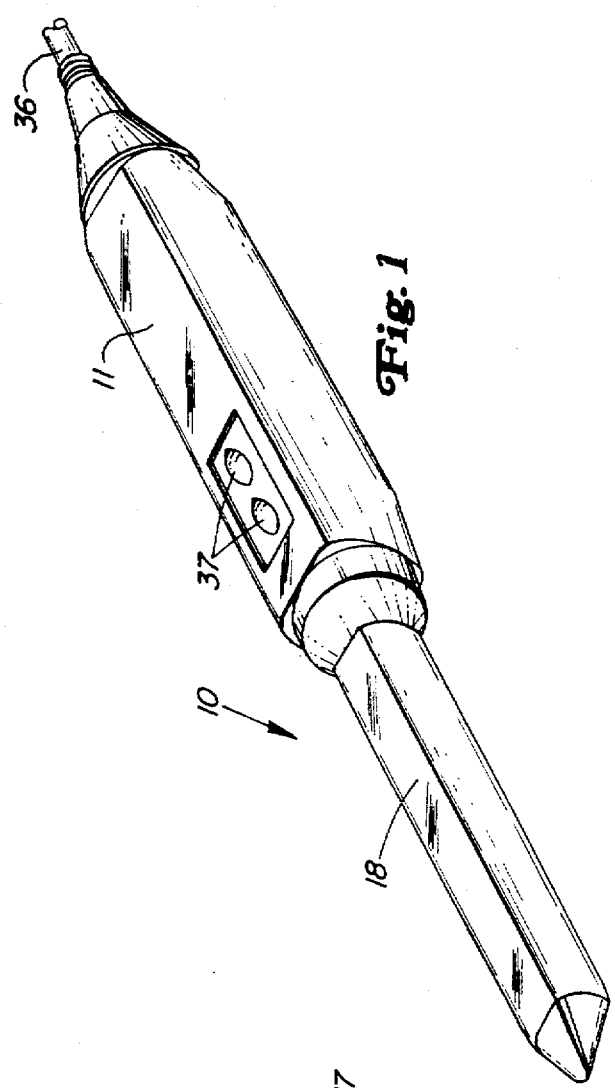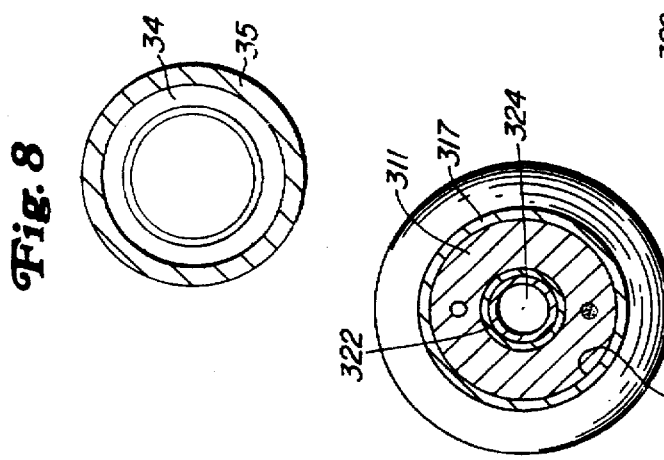

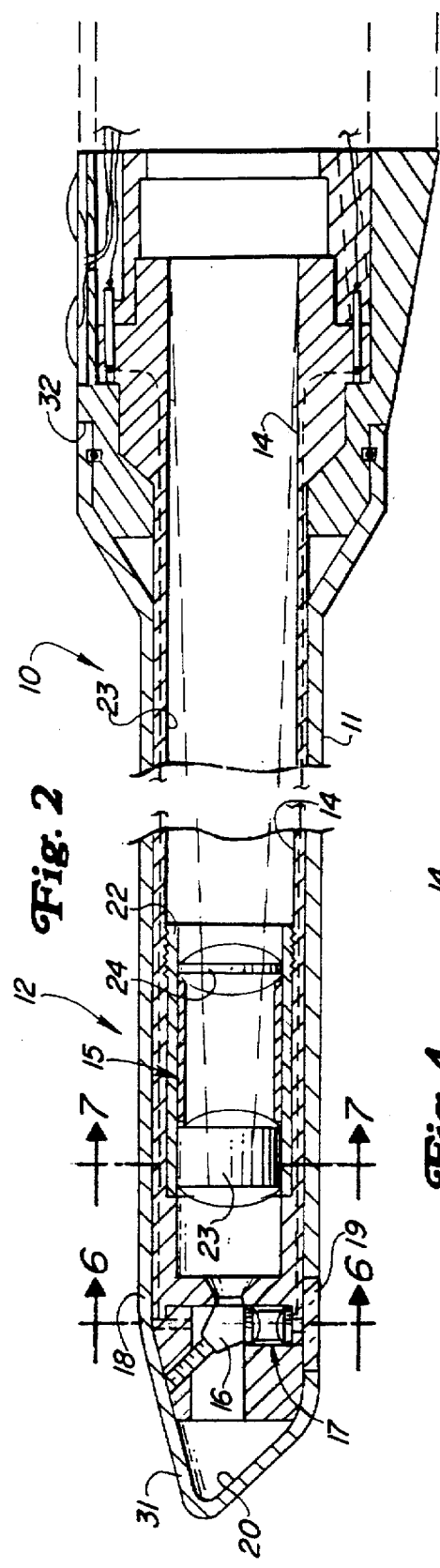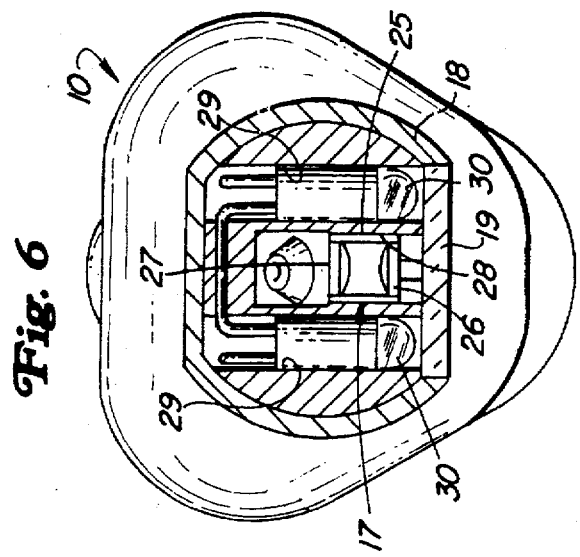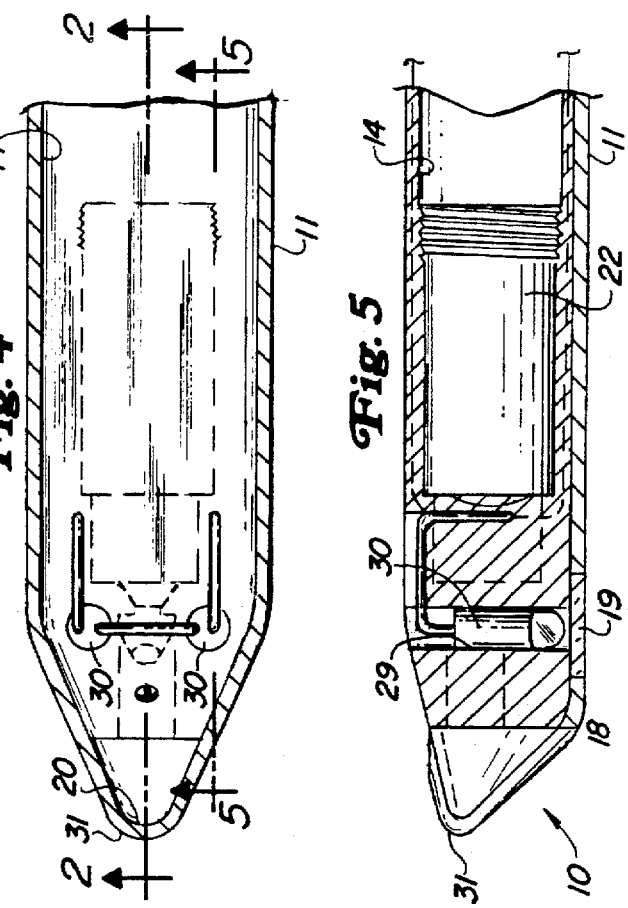

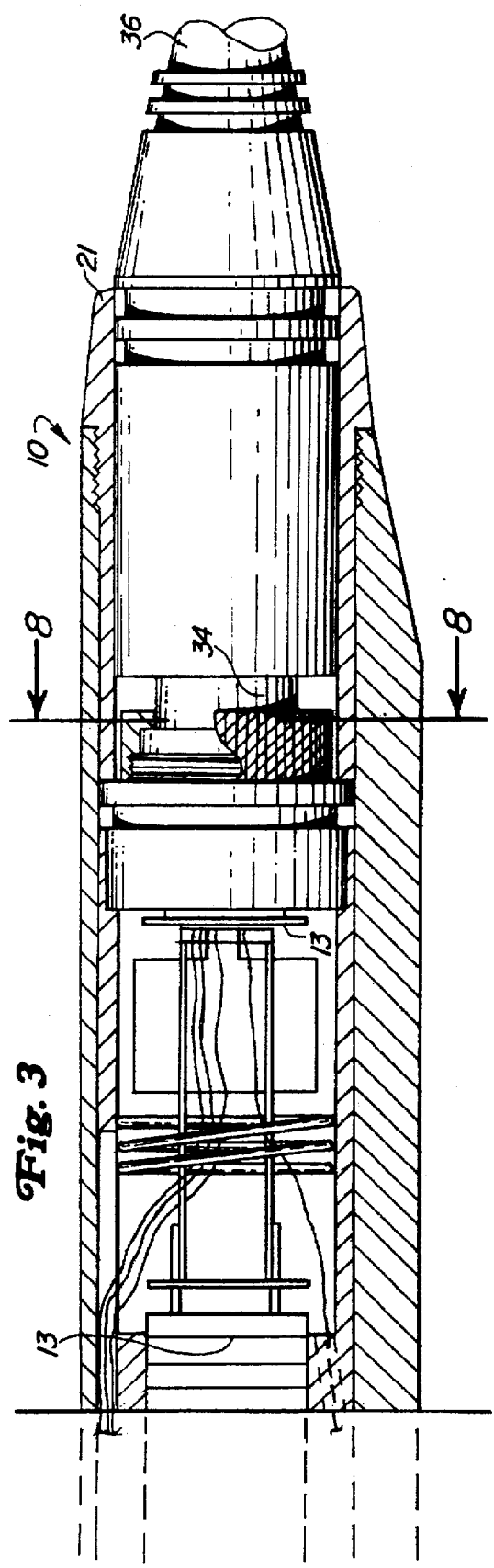
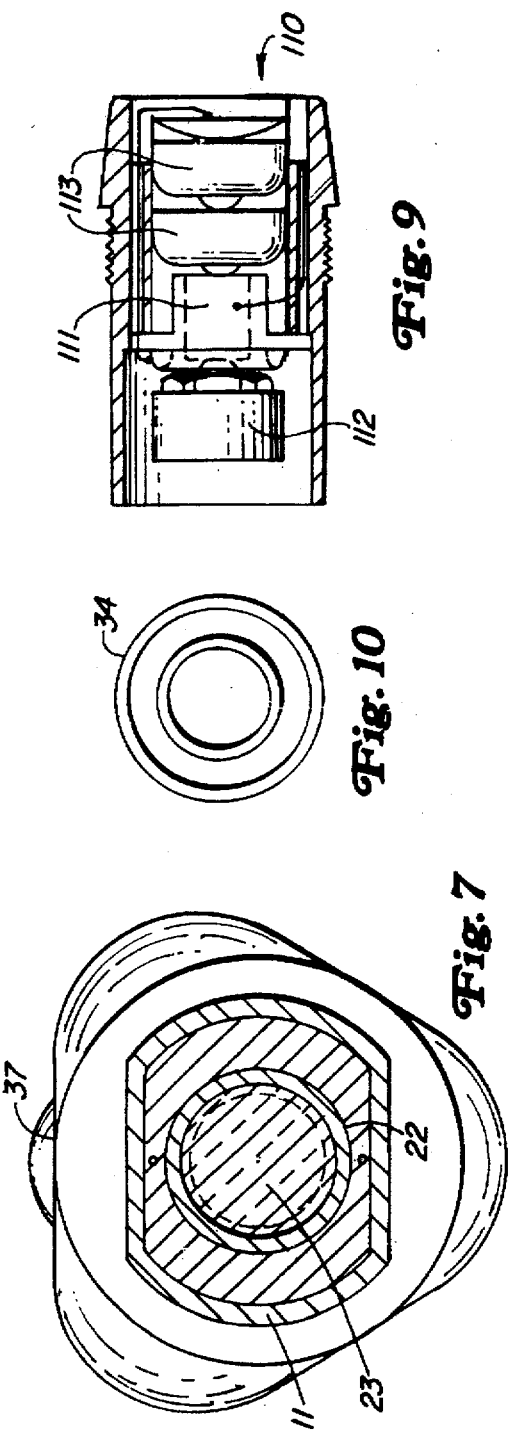

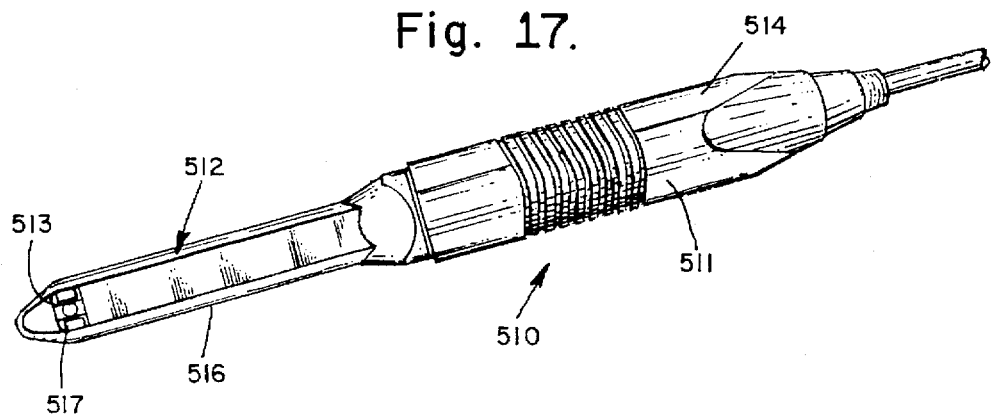
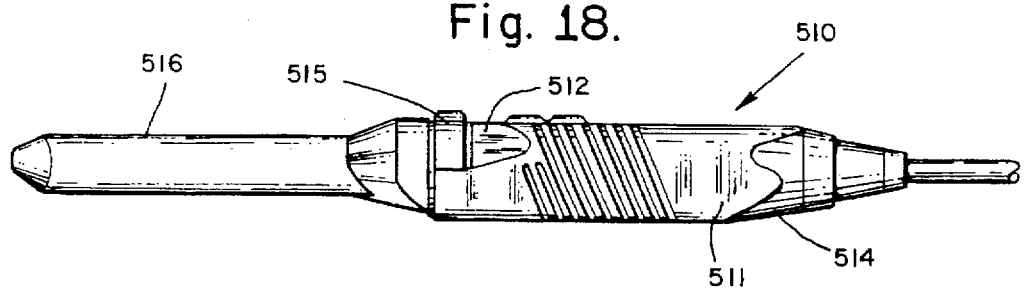
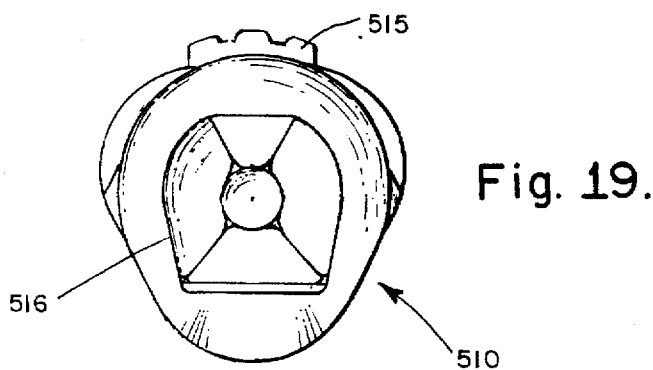

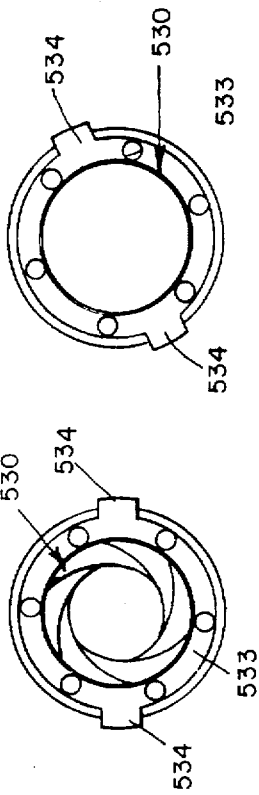
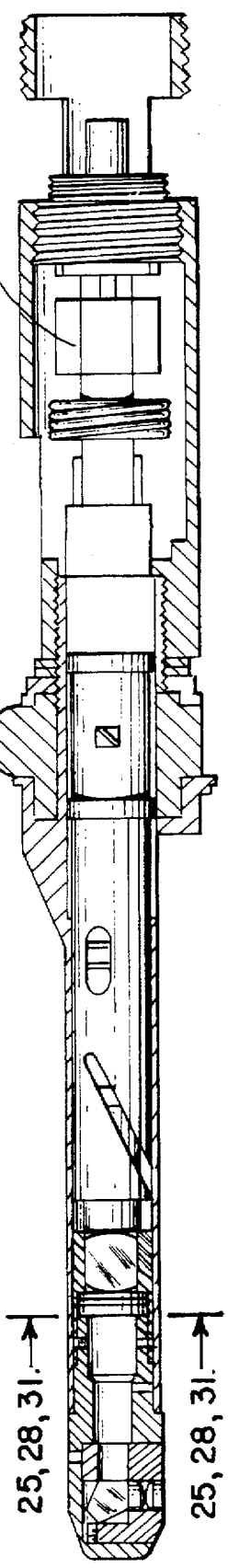
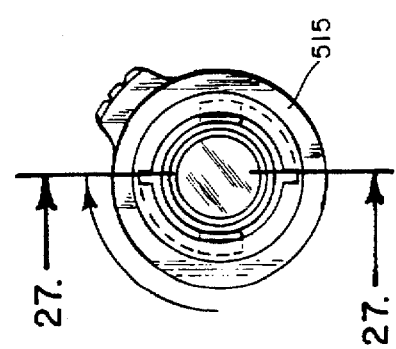
Fig. 28. Fig. 25. Fig. 24. Fig. 20. Fig. 31. Fig. 27. Fig. 26.

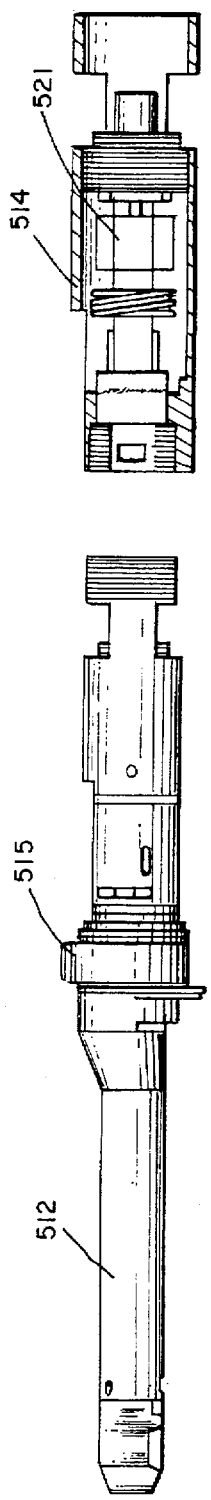
Fig. 21.
Fig. 22.
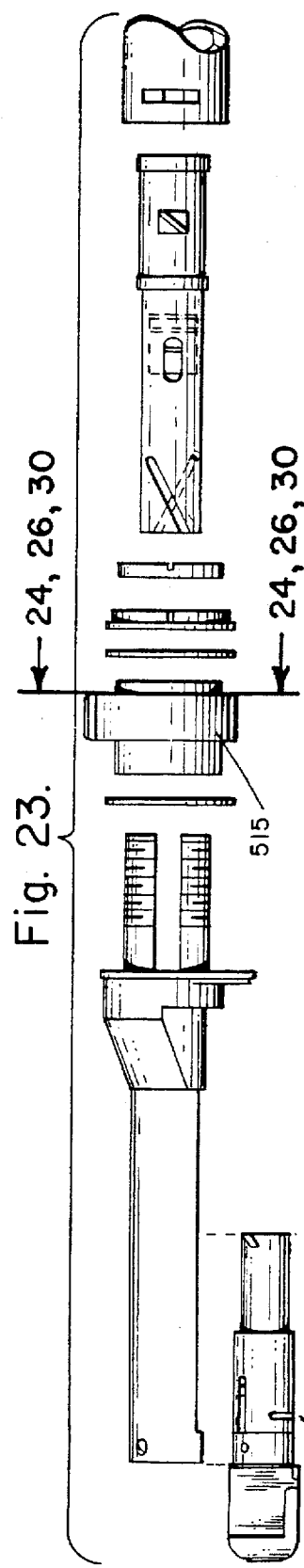
Fig. 23.
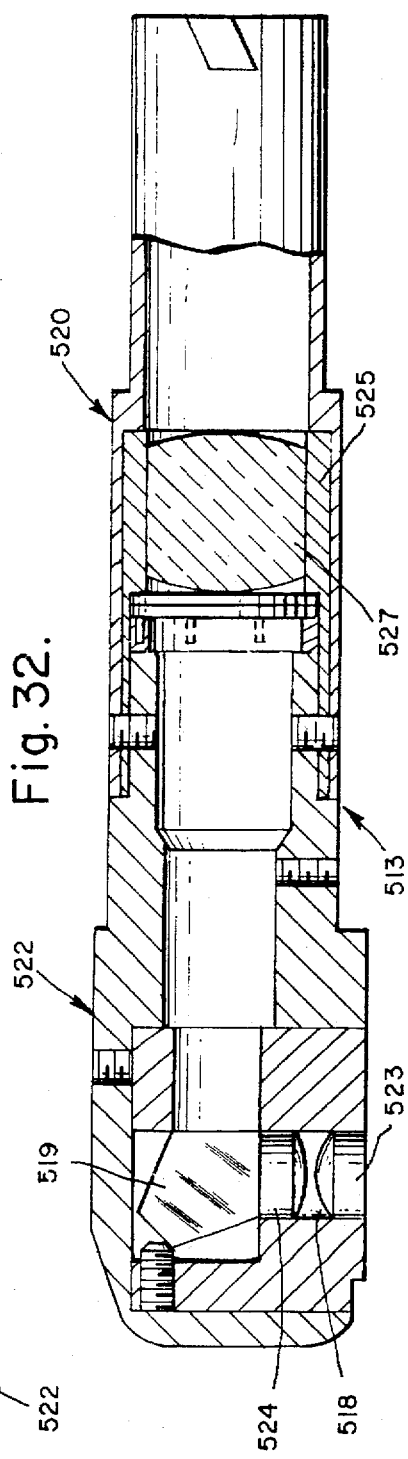
Fig. 32.

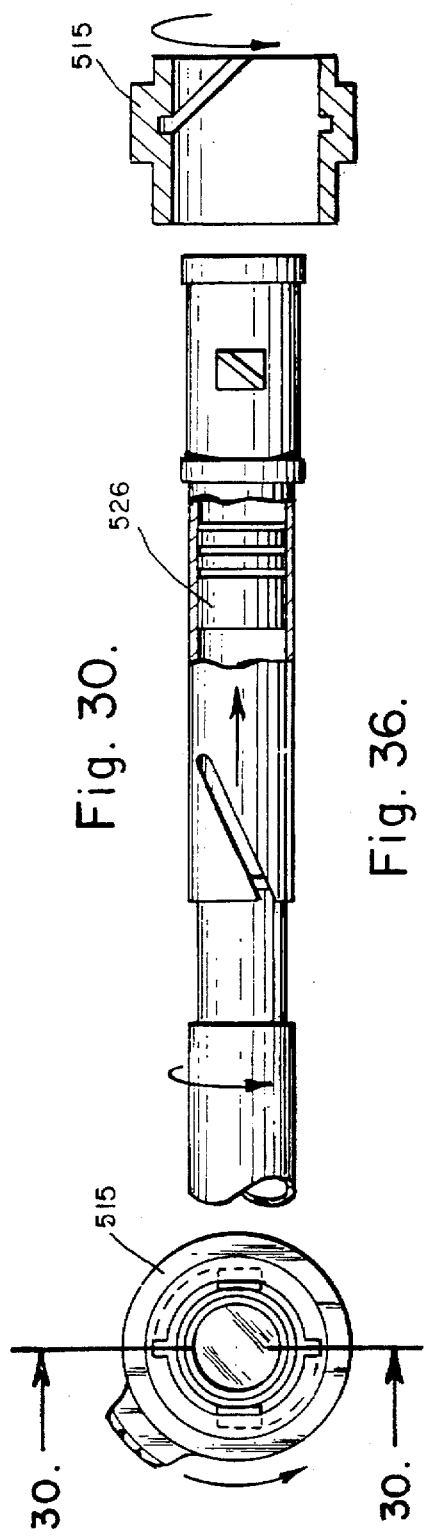

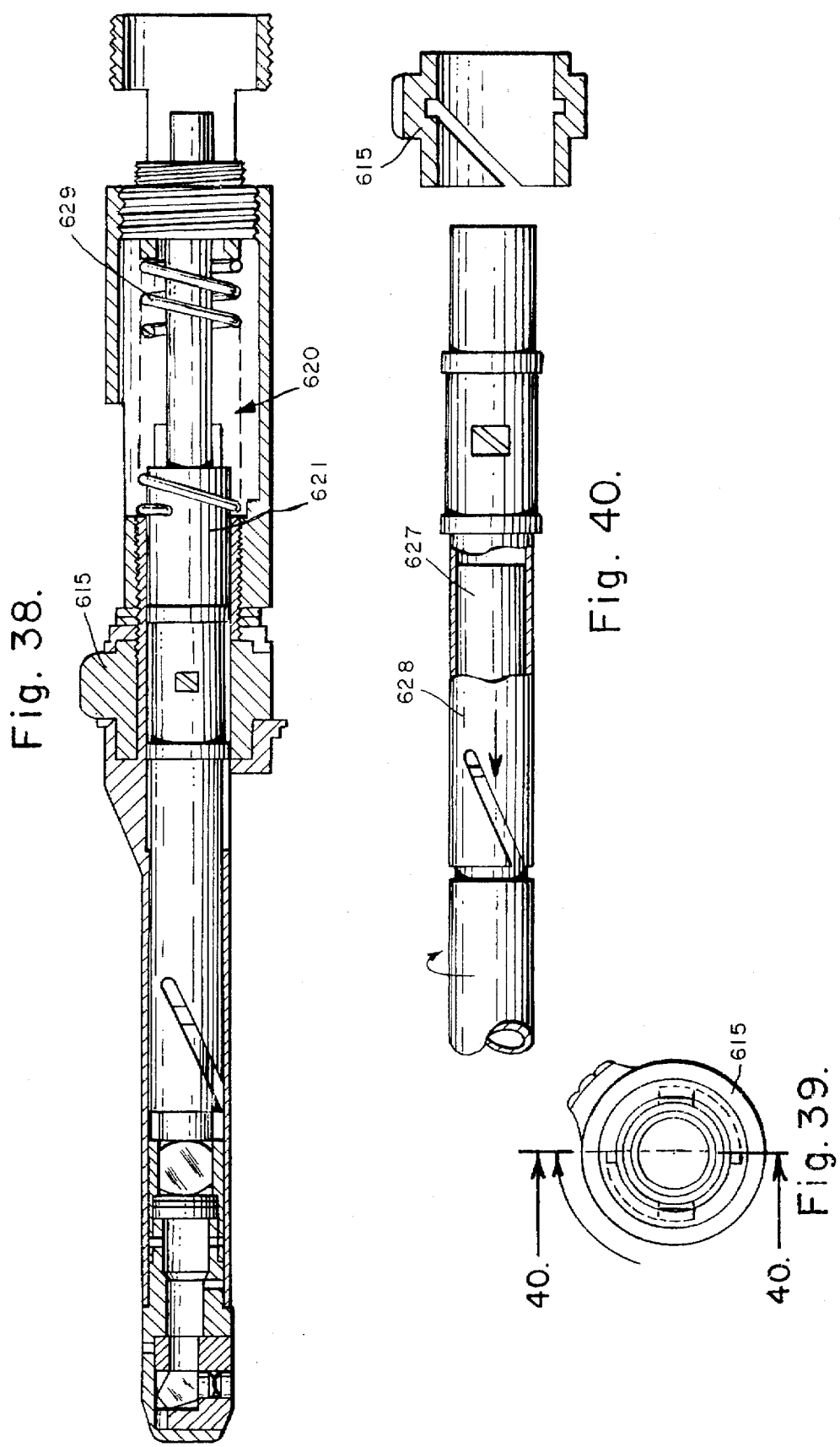

DENTAL VIDEO CAMERA WITH AN ADJUSTABLE IRIS

This is a continuation-in-part of the application filed on Sep. 8, 1994 under Ser. No. 08/303,019 now U.S. Pat. No. 5,525,782 which is a continuation-in-part of the application filed on Sep. 11, 1992 under Ser. No. 07/943,716.

BACKGROUND OF THE INVENTION

The field of the invention is dental video cameras.

U.S. Pat. No. 5,124,797 teaches a dental video camera which includes a proximal housing and a distal module consists of a body containing a magnifying lens, filter and an optical fiber image conduit. The distal module is sterilizable. The proximal housing which is unable to withstand autoclaving does not require sterilization since it does not contact the patient.

U.S. Pat. No. 4,919,114 teaches an endoscope which includes a solid state imaging device and a flexible insertable part for insertion into a body cavity. The solid state imaging device obtains an optical image of an observed part through an observing window provided in a tip part of the flexible insertable part.

U.S. Pat. No. 4,858,001 teaches a hand held endoscopic apparatus which consists of a body, a camera and a removable and interchangeable objective element which is capable of presenting an image of an object to the camera. An optically transparent sheath is capable of isolating the endoscope from the working environment.

U.S. Pat. No. 4,727,416 teaches a video dental camera which includes a handle, a camera head and a mirror. The camera head is located at the distal end of the handle with the camera head being disposed at an angle to the handle.

U.S. Pat. No. 4,757,381 teaches sheaths which are dispensed on a perforated role. Each sheath prevents a dental camera from coming into contact with the patient, while allowing the dental camera to function properly.

U.S. Pat. No. 4,914,521 teaches a sterilizable video camera cover which has a connector and a receptacle. The connector has a guideway for receiving a video camera within a predetermined fixed orientation and serves as a bacteria barrier. The receptacle holds the video camera against a window at the distal end of the connector.

U.S. Pat. No. 4,915,626 teaches a dental video camera which is used to view an image of the interior of the mouth of a patient. The dental video camera displays contemporaneously a video image of the interior of the mouth.

U.S. Pat. No. 4,589,404 teaches a laser endoscope which includes a video camera and an optical system. The video camera transmits an image through the optical system.

U.S. Pat. No. 4,600,939 and U.S. Pat. No. 4,639,772 teach a highly compact focusable video camera which includes an optical system, a sensor-converter and a video electronic processing circuit. The sensor-converter receives an optical image passing through the optical system and converts the optical image to an unprocessed video signal. The video electronic processing circuit processes the unprocessed video signal.

U.S. Pat. No. 4,837,615 teaches a hand held optical probe which includes a light source, two bundles of optical fibers for directing light axially into a fastener hole. The tip end of the bundles being directed at a right angle to the axis of the fastener hole so that the panel edges are illuminated.

SUMMARY OF INVENTION

The present invention is generally directed to a dental video camera including a housing with an elongated cavity, an adjustably focusing lens and CCD camera system and a fixed focusing lens system and a sheath which has a distal end with an optical window and a proximal end into which the housing is inserted. The adjustably focusing lens and CCD camera system and the fixed focusing lens system are all disposed in the housing.

In a first aspect of the present invention, the dental video camera includes an adjustable iris which is optically and mechanically coupled to the adjustably focusing lens system. The adjustably focusing lens and CCD camera system provides a focusing adjustment between a near field of focus and a far field of focus. The adjustable iris is adjusted between a nearly closed opening and a wide open opening in response to the focusing adjustment between the near field of focus and the far field of focus.

In a second aspect of the present invention, the dental video camera includes a light source which is disposed in the elongated cavity of the housing.

In a third aspect of the present invention, the light source is at least one lamp which provides direct illumination.

In a fourth aspect of the present invention, the light source is a combination of at least one lamp and at least one bundle of optical fibers.

In a fifth aspect of the present invention, the optical window is optically matched to the fixed focusing system.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

BRIEF DESCRIPTION OF THE DRAWINGS

FIG. 1 is a perspective view of a dental video camera in accordance with the first embodiment.

FIG. 2 is a side elevational view in cross-section of a fragmented distal portion of the dental video camera of FIG. 1 taken along the line 2—2 of FIG. 4.

FIG. 3 is a side elevational view in cross-section of the proximal portion of the dental video camera of FIG. 1 taken along the line 3—3 of FIG. 4.

FIG. 4 is a top plan view in cross-section of the fragmented distal portion of the dental video camera of FIG. 1 taken along the line 4—4 of FIG. 2.

FIG. 5 is a cross-sectional view of the fragmented distal portion of the dental video camera of FIG. 1 taken along the line 5—5 of FIG. 4.

FIG. 6 is a cross-sectional view of the dental video camera of FIG. 1 taken along the line 6—6 of FIG. 2.

FIG. 7 is a cross-sectional view of the dental video camera of FIG. 1 taken along the line 7—7 of FIG. 2.

FIG. 8 is a cross-sectional view of the dental video camera of FIG. 1 taken along the line 8—8 of FIG. 3.

FIG. 9 is a cross-sectional view of a remote control transmitter for use with the dental video camera of FIG. 1 taken along line 9—9 of FIG. 10 in accordance with the second embodiment.

FIG. 10 is a cross-sectional view of the remote control transmitter of FIG. 9.

FIG. 13 is a side elevational view in cross-section of a fragmented distal portion of a dental video camera in accordance with the fourth embodiment.

FIG. 14 is a cross-sectional view of the dental video camera of FIG. 13 taken along the line 14—14 of FIG. 13.

FIG. 15 is a cross-sectional view of the dental video camera of FIG. 13 taken along the line 15—15 of FIG. 13.

FIG. 17 is a perspective view of a dental video camera with an adjustable iris having a sheath, a distal portion and a proximal portion in accordance with the sixth embodiment.

FIG. 18 is a side elevational view of the dental video camera with the adjustable iris of FIG. 17.

FIG. 19 is a distal end view of the dental video camera with the adjustable iris of FIG. 17.

FIG. 20 is a side elevational view in cross-section of an optical system within the distal portion of the dental video camera with the adjustable iris of FIG. 17.

FIG. 21 is a side elevational view of the distal portion of the dental video camera with the adjustable iris of FIG. 17.

FIG. 22 is a side elevational view of the proximal portion of the dental video camera with the adjustable iris of FIG. 17.

FIG. 23 is an exploded side elevational view of the distal portion, including a knob, of the dental video camera with the adjustable iris of FIG. 17.

FIG. 24 is a transverse view in cross-section of the distal portion of the dental video camera with the adjustable iris of FIG. 17 taken along line 24—24 of FIG. 23 when the knob is in a neutral position.

FIG. 25 is a transverse view in cross-section of the iris of the optical system of the distal portion of the dental video camera with the adjustable iris of FIG. 17 taken along line 25—25 of FIG. 20 showing that when the knob is in the neutral position the opening of the iris is between nearly closed and wide open.

FIG. 26 is a transverse view in cross-section of of the distal portion of the dental video camera with the adjustable iris of FIG. 17 taken along line 26—26 of FIG. 23 when the knob has been rotated clockwise forty five degrees from the neutral position.

FIG. 27 is a side elevational view in cross-section of the mechanical system of the distal portion of the dental video camera with the adjustable iris of FIG. 17 taken along line 27—27 of FIG. 26.

FIG. 28 is a transverse view in cross-section of the distal portion of the dental video camera with the adjustable iris of FIG. 17 taken along line 28—28 of FIG. 20 showing that when the knob has been rotated clockwise forty five degrees from the neutral position the opening of the iris is wide open.

FIG. 29 is a transverse view in cross-section of the distal portion of the dental video camera with the adjustable iris of FIG. 17 taken along line 29—29 of FIG. 23 when the knob has been rotated counter-clockwise forty five degrees from the neutral position.

FIG. 30 is a side elevational view in cross-section of the distal portion of the dental video camera with the adjustable iris of FIG. 17 taken along line 30—30 of FIG. 29.

FIG. 31 is a transverse view in cross-section of the distal portion of the dental video camera with the adjustable iris of FIG. 17 taken along line 31—31 of FIG. 20 showing that when the knob has been rotated counterclockwise forty five degrees from the neutral position the opening of the iris is nearly closed.

FIG. 32 is a side elevational view in cross-section of a lens holder, a first sleeve and a second sleeve of the optical system of the dental video camera with the adjustable iris of FIG. 17.

FIG. 33 is a perspective drawing of the first sleeve of FIG. 32.

FIG. 34 is a perspective drawing of the lens holder of FIG. 32.

FIG. 35 is a side elevational view of the lens holder of FIG. 34.

FIG. 36 is a top plan view of a leaf which is one of the six leaves used in forming the iris.

FIG. 37 is a side elevational view of the leaf of FIG. 36.

FIG. 38 is a side elevational view in cross-section of an optical system within the distal portion of a dental video camera with an adjustable iris in accordance with the seventh embodiment.

FIG. 39 is a transverse view in cross-section of of the distal portion of the dental video camera with the adjustable iris of FIG. 38 when the knob has been rotated clockwise forty five degrees from the neutral position.

FIG. 40 is a side elevational view in cross-section of the mechanical system of the distal portion of the dental video camera with the adjustable iris of FIG. 17 taken along line 40—40 of FIG. 39.

DETAILED DESCRIPTION OF THE PREFERRED EMBODIMENTS

Figure 11:
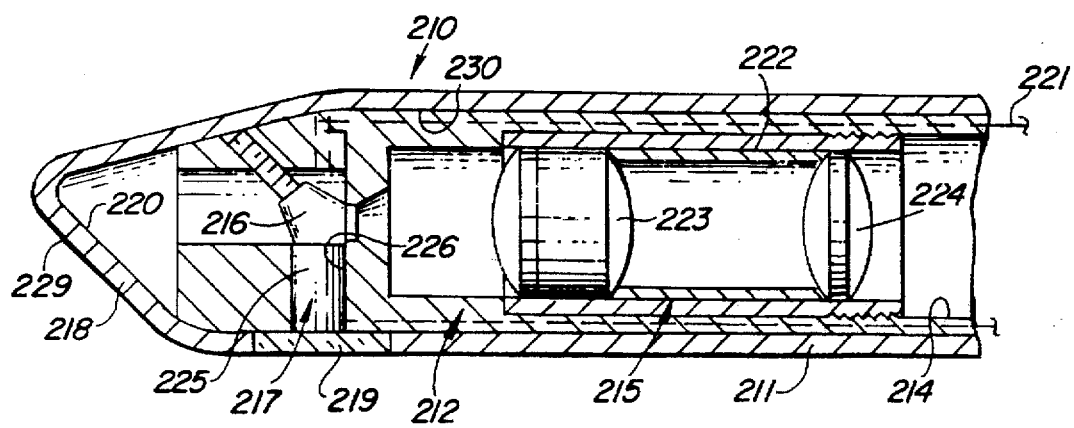
FIG. 11 is a side elevational view in cross-section of a fragmented distal portion of a dental video in accordance with the third embodiment.

Referring to FIG. 1 in conjunction with FIG. 2 and FIG. 3 a dental video camera 10 includes a housing 11, an optical system 12 and a CCD camera 13. The housing 11 has an elongated cavity 14 which has a distal portion and a proximal portion. The optical system 12 is disposed in the distal portion of the elongated cavity 14 of the housing 11. The CCD camera 13 is disposed in the proximal portion of the elongated cavity 14 of the housing 11. The optical system 12 includes an adjustably focusing lens system 15, a pentaprism 16, a fixed focusing lens system 17 and a sheath 18 which has an optical window 19. The housing 11 also has a distal end 20 and a proximal end 21. The pentaprism 16 may be replaced with another optical element which can deflect, deviate, invert or rotate an image. The adjustably focusing lens system 15 includes a first sleeve 22, a first achromatic lens 23 and a second achromatic lens 24. The adjustably focusing lens system 15 may include only a single achromatic lens. The first achromatic lens 23 may be replaced by a singlet lens, a doublet lens or triplet lens. The first and second achromatic lenses 23 and 24 are disposed in the first sleeve 22 and are optically coupled to the CCD camera 13. The adjustably focusing lens system 15 is disposed within the elongated cavity 14 of the housing 11 at the distal end 20.

Referring to FIG. 4 in conjunction with FIG. 5 and FIG. 6 the fixed focusing lens system 17 includes a second sleeve 25, a first microlens 26 and a second microlens 27. The first and second microlenses 26 and 27 are disposed in the second sleeve 25. The pentaprism 16 optically couples the fixed focusing lens system 17 to the adjustably focusing lens system 15. The elongated cavity 14 of the housing 11 has a bore 28 which is orthogonally disposed thereto at the distal end 20 thereof. The fixed focusing lens system 17 is disposed within the bore 28. The housing 11 further has two parallel orthogonally disposed cavities 29 at its distal end 20. The internal surfaces of the two parallel orthogonally disposed cavities 29 may be polished or plated so that they act as reflectors in order to direct heat toward the optical window 19 of the sheath 18 thereby defogging the optical window 19 and minimizing heat build-up within housing 11 at the distal end 20. The dental video camera 10 also includes two lamps 30 which are disposed in the two inwardly angled orthogonally disposed cavities 29 of the housing 11. The housing dissipates heat from the two lamps 30 which provide both direct illumination and anti-fogging control through the optical window 19 of the sheath 18. The sheath 18 has a distal end 31, a proximal end 32 and an elongated cavity 33. The housing 11 is removably inserted into the elongated cavity 33 of the sheath 18.

Referring to FIG. 2 in conjunction with FIG. 3 and FIG. 7 the adjustably focusing lens system 15 is optically coupled to the CCD camera 13. The pentaprism 16 optically couples the fixed focusing lens system 17 to the adjustably focusing lens system 15. The optical window 19 of the sheath 18 is optically aligned and optically coupled to the fixed focusing lens system 17.

Referring to FIG. 3 in conjunction with FIG. 8 the dental video camera 10 further includes a multiple-pin male connector 34, a multiple-pin female connector 35, a cable 36 and external switches 37. The multiple-pin male connector 34 is electrically coupled to the multiple-pin female connector 35. The multiple-pin female connector 35 is electrically coupled to the cable 36. The cable 36 has a plurality of wires which connect the external switches 37 to a video processor, a recording device and a thermal printer to the CCD camera 13 and the two lamps 30 to a power source.

Referring to FIG. 9 in conjunction with FIG. 3 and FIG. 10 a dental video camera 110 includes a remote control transmitter 111 with a multiple-pin female connector 112 and two batteries 113. The batteries 113 are either rechargeable or replaceable and are a source of power to the two lamps 30. The multiple-pin male connector 34 is electrically coupled to the multiple-pin female connector 112 of the remote control transmitter 111. A receiver remotely couples the thermal printer, the video processor and the recording device to the remote control transmitter 111 so that one of the external switches 37 controls each of the thermal printer, the video processor and the recording device.

Figure 12:
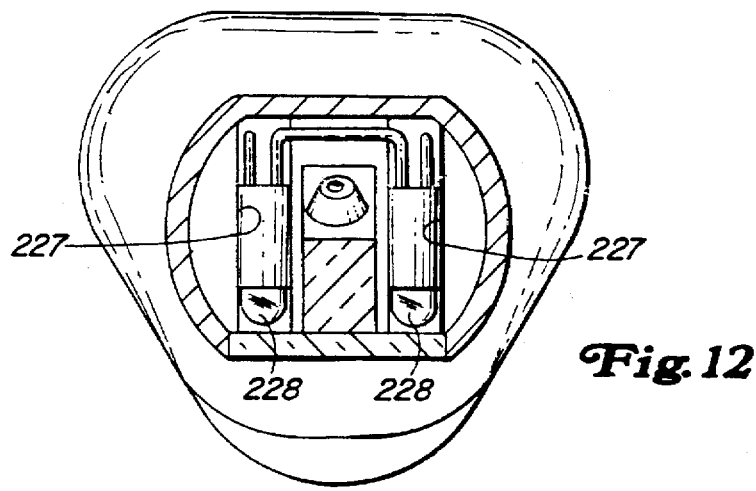
FIG. 12 is a cross-sectional view of the dental video camera of FIG. 11 taken along the line 12—12 of FIG. 11.

Referring to FIG. 11 in conjunction with FIG. 12 a dental video camera 210 includes a housing 211, an optical system 212 and a CCD camera. The housing 211 has an elongated cavity 214 which has a distal portion and a proximal portion. The optical system 212 is disposed in the distal portion of the elongated cavity 214 of the housing 211. The CCD camera is disposed in the proximal portion of the elongated cavity 214 of the housing 211. The optical system 212 includes a adjustably focusing lens system 215, a pentaprism 216, a fixed focusing lens system 217 and a sheath 218 which has an optical window 219. The housing 211 also has a distal end 220 and a proximal end 221. The adjustably focusing lens system 215 includes a first sleeve 222, a first achromatic lens 223 and a second achromatic lens 224. The first achromatic lens 223 may be replaced by singlet lens, a doublet lens or a triplet lens. The first and second achromatic lenses 223 and 224 are disposed in the first sleeve 222 and are optically coupled to the CCD camera. The adjustably focusing lens system 215 is disposed within the elongated cavity 214 of the housing 211 at the distal end 220. The pentaprism 216 may be replaced with another optical element which can deflect, deviate, invert or rotate an image. The fixed focusing lens system 217 includes a gradient indexed lens 225. The pentaprism 216 optically couples the fixed focusing lens system 217 to the adjustably focusing lens system 215. The elongated cavity 214 of the housing 211 has a bore 226 which is orthogonally disposed thereto at the distal end 220 thereof. The fixed focusing lens system 217 is disposed within the bore 226. The housing 211 further has two parallel orthogonally disposed cavities 227 at its distal end 220. The dental video camera 210 also includes two lamps 228 which are disposed in the two parallel orthogonally disposed cavities 229 of the housing 211. The two lamps 228 provide direct illumination through the optical window 219 of the sheath 218. The sheath 218 has a distal end 229, a proximal end and an elongated cavity 230. The housing 211 is removably inserted into the elongated cavity 230 of the sheath 218. The adjustably focusing lens system 215 is optically coupled to the CCD camera. The pentaprism 216 optically couples the fixed focusing lens system 217 to the adjustably focusing lens system 215. The optical window 219 of the sheath 218 is optically aligned and optically coupled to the fixed focusing lens system 217.

Referring to FIG. 13 in conjunction with FIG. 14 and FIG. 15 a dental video camera 310 includes a housing 311, an optical system 312 and a CCD camera. The housing 311 has an elongated cavity 314 which has a distal portion and a proximal portion. The optical system 312 is disposed in the distal portion of the elongated cavity 314 of the housing 311. The CCD camera is disposed in the proximal portion of the elongated cavity 314 of the housing 311. The optical system 312 includes a adjustably focusing lens system 315, a fixed focusing lens system 316 and a sheath 317 which has an optical window 318. The housing 311 also has a distal end 319 and a proximal end. The adjustably focusing lens system 315 includes a first sleeve 320, a first achromatic lens and a second achromatic lens 321. The first achromatic lens may be replaced by a singlet lens, a doublet lens or a triplet lens. The first and second achromatic lenses 321 are disposed in the first sleeve 320 and are optically coupled to the CCD camera. The adjustably focusing lens system 315 is disposed within the elongated cavity 314 of the housing 311 at the distal end 319. The fixed focusing lens system 316 includes a second sleeve 322, a first microlens 323 and a second microlens 324. The first and second microlenses 323 and 324 are disposed in the second sleeve 322. The fixed focusing lens system 316 is optically coupled to the adjustably focusing lens system 315. The elongated cavity 314 of the housing 311 has a bore 325 which is axially aligned therewith at the distal end 319 thereof. The fixed focusing lens system 316 is disposed within the bore 325. The housing 311 further has two parallel cavities 326 disposed at its distal end 319. The dental video camera 310 also includes two lamps 327 and two bundles 328 of optical fibers both of which are disposed in the two parallel cavities 326 of the housing 311. The two lamps 327 provide light to the bundles 328 of optical fibers which provide direct illumination through the optical window 318 of the sheath 317. The sheath 317 has a distal end 329, a proximal end and an elongated cavity 330. The housing 311 is removably inserted into the elongated cavity 330 of the sheath 317. The adjustably focusing lens system 315 is optically coupled to the CCD camera. The fixed focusing lens system 316 is optically coupled to the adjustably focusing lens system 315. The optical window 318 of the sheath 317 is optically aligned and optically coupled to the fixed focusing lens system 316.

Figure 16:
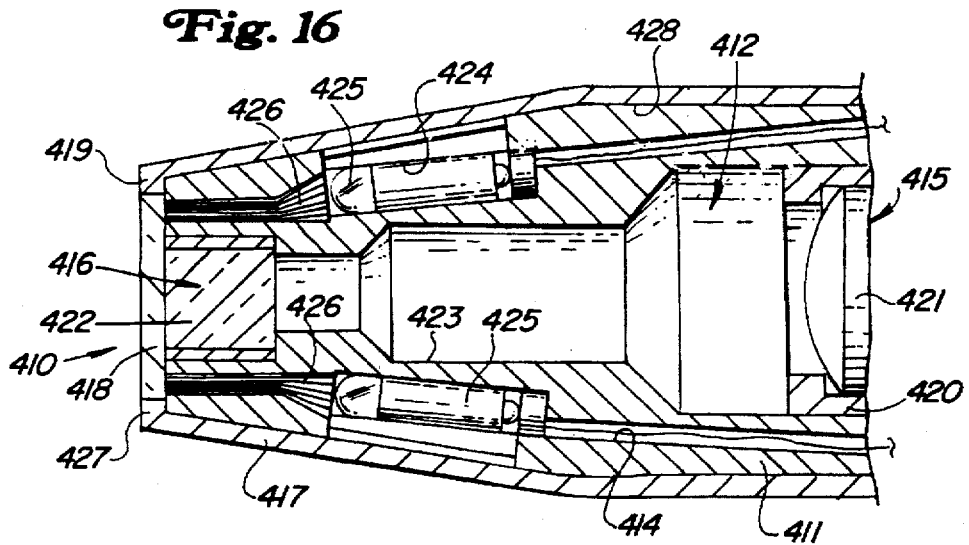
FIG. 16 is a side elevational view in cross-section of a fragmented distal portion of a dental video camera in accordance with the fifth embodiment.

Referring to FIG. 16 a dental video camera 410 includes a housing 411, an optical system 412 and a CCD camera. The housing 411 has an elongated cavity 414 which has a distal portion and a proximal portion. The optical system 412 is disposed in the distal portion of the elongated cavity 414 of the housing 411. The CCD camera is disposed in the proximal portion of the elongated cavity 414 of the housing 411. The optical system 412 includes a adjustably focusing lens system 415, a fixed focusing lens system 416 and a sheath 417 which has an optical window 418. The housing 411 also has a distal end 419 and a proximal end. The adjustably focusing lens system 415 includes a first sleeve 420, a first achromatic lens and a second achromatic lens 421. The first achromatic lens may be replaced by a singlet lens, a doublet lens or a triplet lens. The first and second achromatic lenses 421 are disposed in the first sleeve 420 and are optically coupled to the CCD camera. The adjustably focusing lens system 415 is disposed within the elongated cavity 414 of the housing 411 at the distal end 419. The fixed focusing lens system 416 includes a gradient indexed lens 422. The fixed focusing lens system 416 is optically coupled to the adjustably focusing lens system 415. The elongated cavity 414 of the housing 411 has a bore 423 which is axially aligned therewith at the distal end 419 thereof. The fixed focusing lens system 416 is disposed within the bore 423. The housing 411 further has two parallel cavities 424 disposed at its distal end 419. The dental video camera 410 also includes two lamps 425 and two bundles 426 of optical fibers both of which are disposed in the two parallel cavities 424 of the housing 411. The two lamps 425 provide light to the bundles 426 of optical fibers which provide direct illumination through the optical window 418 of the sheath 417. The sheath 417 has a distal end 427, a proximal end and an elongated cavity 428. The housing 411 is removably inserted into the elongated cavity 428 of the sheath 417. The adjustably focusing lens system 415 is optically coupled to the CCD camera. The fixed focusing lens system 416 is optically coupled to the adjustably focusing lens system 415. The optical window 418 of the sheath 417 is optically aligned and optically coupled to the fixed focusing lens system 416.

Referring to FIG. 17 in conjunction with FIG. 18 and FIG. 19 a dental video camera 510 includes a housing 511 having a distal portion 512 with an optical system 513 and a proximal portion 514, a knob 515 and a sheath 516 with an optical window 517. The sheath 516 is formed out of a transparent material with a known index of refraction. The transparent material may be either glass or a plastic. The dental video camera 510 may also includes a light source which is mechanically disposed in the elongated cavity of the housing 511. The light source has an output at the distal end of the housing 511. The light source may have at least one lamp which provide direct illumination. The light source may also include either at least one bundle of optical fibers optically coupled to the lamp or a rod formed out of transparent material having a gradient refraction index. The dental video camera 510 may further includes a remote control transmitter coupled to the CCD camera 521.

Referring to FIG. 20 in conjunction with FIG. 21 and FIG. 22 the optical system 513 includes a fixed focusing lens system 518, a pentaprism 519, an adjustably focusing lens system 520 and a CCD camera 521. The distal portion 512 of the housing 511 has a nose piece 522. The fixed focusing lens system 518 includes a first microlens 523 and a second microlens 524 which are disposed within the nose piece 522. The optical window 517 of the sheath 516 is optically aligned with the first and second microlenses 523 and 524 of the fixed focusing system 518 and optically matched to the fixed focusing system 518. The pentaprism 519 optically couples the fixed focusing lens system 518 to the adjustably focusing lens system 520. The pentaprism 519 may be replaced with any other optical element which can fold, deflect, deviate, invert or rotate an image. The CCD camera 521 is disposed within the proximal portion 513 of the housing 511. The adjustably focusing lens system 520 provides a focusing adjustment between a near field of focus and a far field of focus.

Referring to FIG. 20 in conjunction with FIG. 22 and FIG. 23 the adjustably focusing lens system 520 includes a first sleeve 525 and a second sleeve 526. The first sleeve 525 has a longitudinal axis. The first sleeve 525 is axially aligned along the longitudinal axis and is disposed within the elongated cavity of the housing 511 adjacent to the fixed focusing lens system 520. The first sleeve 525 is able to rotate about the longitudinal axis and is restrained from moving laterally back and forth along the longitudinal axis. The second sleeve 526 is telescopically and slidably coupled to the first sleeve 525. The second sleeve 526 is able to move laterally back and forth along the longitudinal axis and is restrained from rotating about the longitudinal axis. In the present embodiment the knob 515 bi-directionally drives the second sleeve 526 laterally to produce back and forth lateral movements along the longitudinal axis; in other embodiments a slide mechanism may bi-directionally drives the second sleeve 526 laterally to produce back and forth lateral movements along the longitudinal axis. The back and forth lateral movements of the second sleeve 526 generates clockwise and counter-clockwise rotations, respectively, of the first sleeve 525. The adjustably focusing lens system 520 also includes a first achromatic lens, which is disposed in a first lens carrier 527, and a second achromatic lens, which is disposed in a second lens carrier 528. The second lens carrier 528 with the second achromatic lens is disposed within the second sleeve 526 and is fixedly coupled to the second sleeve 526. The back and forth lateral movements of the second sleeve 526 changes the position of the first achromatic lens with respect to the second achromatic lens.

Referring to FIG. 23 in conjunction with FIG. 24 and FIG. 25 the dental video camera also includes an adjustable iris 530 which is optically and mechanically coupled to the adjustably focusing lens system 520. The adjustable iris 530 is adjusted between a nearly closed opening and a wide open opening in response to the focusing adjustment between a near field of focus and a far field of focus. When the knob 515 is in the neutral position the opening of the adjustable iris 530 is between nearly closed and wide open.

Referring to FIG. 23 in conjunction with FIG. 26, FIG. 27 and FIG. 28 when the knob 515 has been rotated counter-clockwise forty five degrees from the neutral position the opening of the adjustable iris 530 is wide open.

Referring to FIG. 23 in conjunction with FIG. 29, FIG. 30 and FIG. 31 when the knob 515 has been rotated clockwise forty five degrees from the neutral position the opening of the adjustable iris 530 is counter-clockwise forty five degrees from the neutral position the opening of the adjustable iris 530 is nearly closed.

Referring to FIG. 32 in conjunction with FIG. 20 the adjustable iris 530 includes a lens holder 531, six leaves 532 and a ring 533 with two wings 534. The lens holder 531 is disposed in the first sleeve 525.

Referring to FIG. 33 in conjunction with FIG. 32 the first sleeve 525 has two transverse slots 535 and two partial, circumferencial radial slots 536.

Referring to FIG. 34 in conjunction with FIG. 32 and FIG. 35 the lens holder 531 has two transverse slots 537, six radial slots 538 in the present embodiment and two radial slots 539; in other embodiments there are as many radial slots as there are leaves. The first lens carrier 527 with the first achromatic lens is disposed within the lens holder 531 and is fixedly coupled to the lens holder 531. The lens holder 531 is disposed within and coupled to the first sleeve 525. In the present embodiment there are six leaves 540 which form the adjustable iris 530; in other embodiments there may be any number of leaves ranging from at least two to twenty four. The ring 533 with the two wings 534 and the six leaves 540 are disposed within the lens holder 531.

Referring to FIG. 36 in conjunction with FIG. 35 and FIG. 37 each leaf 540 has a first end with a first pin 541 and a second end with a second pin 542. The first pin 541 of each leaf 540 is disposed in one of the radial slots 538 within the lens holder 531. The ring 533 has six pin holes 543. The second pins 542 are disposed in the pin holes 543. The ring 533 is disposed within and rotatably coupled to the lens holder 531. The two transverse slots 537 of the lens holder 531 allow the two wings 534 of the ring 533 not only to pass when the ring 533 is slided into the first sleeve 525 in order to secure the six leaves 540, but also to rotate forty five degrees in either a clockwise direction or a counter-clockwise direction. The two transverse slots 535 of the first sleeve 525 are mechanically coupled to the two wings 534 of the ring 533 so that when the first sleeve 525 is rotated it rotates the ring 533.

Referring to FIG. 38 the dental video camera 610 also includes a housing 611, which has a distal portion 612 and a proximal portion 613, and an optical system 614 which includes a knob 615, a sheath, which has an optical window, a fixed focusing lens system 618, a pentaprism 619, an adjustably focusing lens and CCD camera system 620 which includes a CCD camera 621. The CCD camera 621 is disposed within and slidably coupled to the elongated cavity of the housing 611 at the proximal end 613 thereof. The distal portion 612 of the housing 611 has a nose piece 622. The fixed focusing lens system 618 includes a first microlens 623 and a second microlens 624 which are disposed within the nose piece 622. The optical window 617 of the sheath 616 is optically aligned with the first and second microlenses 623 and 624 of the fixed focusing system 618 and optically matched to the fixed focusing system 618. The pentaprism 619 optically couples the fixed focusing lens system 618 to the adjustably focusing lens and CCD camera system 620. The pentaprism 619 may be replaced with any other optical element which can fold, deflect, deviate, invert or rotate an image.

Referring to FIG. 38 in conjunction with FIG. 39 and FIG. 40 the dental video camera 610 also includes an adjustably focusing lens and CCD camera system 620 which is disposed within the proximal portion 613 of the housing 611. The adjustably focusing lens and CCD camera system 620 also includes a first sleeve 625 and a second sleeve 626. The first sleeve 625 has a longitudinal axis. The first sleeve 625 is axially aligned along the longitudinal axis and is disposed within the elongated cavity of the housing 611 adjacent to the fixed focusing lens system 620. The first sleeve 625 is able to rotate about the longitudinal axis and is restrained from moving laterally back and forth along the longitudinal axis. The second sleeve 626 is telescopically and slidably coupled to the first sleeve 625. The second sleeve 626 is able to move laterally back and forth along the longitudinal axis and is restrained from rotating about the longitudinal axis. In the present embodiment the knob 615 bi-directionally drives the second sleeve 626 laterally to produce back and forth lateral movements along the longitudinal axis; in other embodiments a slide mechanism may bi-directionally drives the second sleeve 626 laterally to produce back and forth lateral movements along the longitudinal axis. The back and forth lateral movements of the second sleeve 626 generates clockwise and counter-clockwise rotations, respectively, of the first sleeve 625. The adjustably focusing lens and CCD camera system 620 also includes a first achromatic lens, which is disposed in a first lens carrier 627, and a second achromatic lens, which is disposed in a second lens carrier 628. The first lens carrier 627 with the first achromatic lens is disposed within and coupled to the first sleeve 625. The second lens carrier 628 with the second achromatic lens is disposed within the first sleeve 625 and is fixedly coupled to the first sleeve 625. The adjustably focusing lens and CCD camera system 620 further includes a spring 629. The spring 629 resiliently couples the CCD camera 621 to the elongated cavity of the housing 611. The second sleeve 626 engages the CCD camera 621 in order to laterally move the CCD camera 621 back and forth. The back and forth lateral movements of the second sleeve 626 changes the position of the CCD camera 621 with respect to the first and second achromatic lenses thereby changing the field of focus. The adjustably focusing lens and CCD camera system 620 provides a focusing adjustment between a near field of focus and a far field of focus. The dental video camera 610 also includes an adjustable iris 630 which is optically and mechanically coupled to the adjustably focusing lens system 620. The adjustable iris 630 is adjusted between a nearly closed opening and a wide open opening in response to the focusing adjustment between the near field of focus and the far field of focus. When the knob 615 is in the neutral position the opening of the adjustable iris 630 is between nearly closed and wide open.

Referring to FIG. 39 in conjunction with FIG. 40 when the knob 615 has been rotated counter-clockwise forty five degrees from the neutral position the opening of the adjustable iris 630 is wide open.

From the foregoing it can be seen that a dental video camera with an adjustable iris has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed:

1. A dental video camera comprising:
   a. a housing having an elongated cavity with a distal end and a proximal end;
   b. an adjustably focusing lens and CCD camera system disposed within said elongated cavity of said housing whereby said adjustably focusing lens and CCD camera system provides a focusing adjustment between a near field of focus and a far field of focus;
   c. a fixed focusing lens system optically coupled to said adjustably focusing lens and CCD camera system and disposed in said elongated cavity of said housing adjacent to said distal end thereof; and
   d. an adjustable iris optically and mechanically coupled to said adjustably focusing lens and CCD camera system whereby said adjustable iris is adjusted between a nearly closed opening and a wide open opening in response to said focusing adjustment between said near field of focus and said far field of focus.

2. A dental video camera according to claim 1 wherein said dental video camera includes a light source disposed in said elongated cavity of said housing and said housing having at said distal end thereof an output window optically coupled to said light source.

3. A dental video camera according to claim 1 wherein said dental video camera includes a sheath having a distal end and a proximal end into which said housing is inserted, said sheath having at said distal end thereof an optical window whereby said fixed focusing lens system is optically aligned with said optical window.

4. A dental video camera according to claim 3 wherein said optical window of said sheath is optically matched to said fixed focusing system.

5. A dental video camera according to claim 1 wherein said dental video camera includes:
 a. a light source mechanically disposed in said elongated cavity of said housing, said light source having an output at said distal end of said housing; and
 b. a sheath having a distal end and a proximal end into which said housing is inserted, said sheath having at said distal end thereof an optical window whereby said fixed focusing lens system is optically aligned with said optical window.

6. A dental video camera according to claim 5 wherein said optical window of said sheath is optically matched to said fixed focusing system.

7. A dental video camera according to claim 1 wherein said adjustable iris is rotatably adjustable and said adjustably focusing lens and CCD camera system includes:
 a. a CCD camera disposed within and slidably coupled to said elongated cavity of said housing at said proximal end thereof;
 b. a spring resiliently coupling said CCD camera to said to said elongated cavity of said housing;
 c. a first sleeve having a longitudinal axis, said first sleeve being axially aligned along said longitudinal axis and being disposed within said elongated cavity of said housing adjacent to said fixed focusing lens system, said first sleeve being able to rotate about said longitudinal axis and being restrained from moving laterally back and forth along said longitudinal axis;
 d. a first lens carrier with a first achromatic lens disposed within said first sleeve and fixedly coupled to said first sleeve;
 e. a second sleeve telescopically and slidably coupled to said first sleeve, said second sleeve being able to move laterally back and forth along said longitudinal axis and being restrained from rotating about said longitudinal axis;
 f. a second lens carrier with a second achromatic lens disposed within said first sleeve and fixedly coupled to said first sleeve whereby said second sleeve engages said CCD camera so that said second sleeve laterally moves said CCD camera back and forth in order to change the position of said CCD camera with respect to said first and second achromatic lenses thereby changing the field of focus; and
 g. a mechanism for bi-directionally driving said second sleeve laterally to produce back and forth lateral movements along said longitudinal axis whereby said back and forth lateral movements of said second sleeve generates clockwise and counter-clockwise rotations, respectively, of said first sleeve thereby rotatably adjusting said adjustable iris between said nearly closed opening thereof and said wide open opening thereof.

8. A dental video camera according to claim 7 wherein said first sleeve has two partial, circumferencial slots and two transverse slots and wherein said adjustable iris includes:
 a. lens holder having at least one transverse slot, a plurality of radial slots and at least one partial, circumferencial slots, said first lens carrier with said first achromatic lens being disposed within said lens holder and being fixedly coupled thereto and said lens holder being disposed within said first sleeve;
 b. a plurality of leaves each of which has a first end with a first pin and a second end with a second pin whereby said first pins are disposed in said radial slots within said lens holder; and
 c. a ring having a plurality of pin holes and at least one wing, said ring being disposed within and rotatably coupled to said lens holder whereby said second pins are disposed in said pin holes and whereby said transverse slot allows said wing of said ring to pass when said ring is slided into said first sleeve in order to secure said leaves.

9. A dental video camera according to claim 2 wherein said light source is at least one lamp which provide direct illumination.

10. A dental video camera according to claim 2 wherein said dental video camera includes a pentaprism which optically couples said adjustably focusing lens and CCD camera system to said fixed focusing lens system and which is disposed in said elongated cavity of said housing at said distal end.

11. A dental video camera according to claim 2 wherein said fixed focusing lens system includes:
 a. a lens holder disposed in said elongated cavity of said housing adjacent to said output window at said distal end;
 b. a first microlens disposed in said lens holder; and
 c. a second microlens optically aligned with said first microlens and disposed in said lens holder.

12. A dental video camera according to claim 2 wherein said light source includes:
 a. at least one lamp disposed in said elongated cavity;
 b. at least one bundle of optical fibers optically coupled to said lamp.

13. A dental video camera according to claim 2 wherein said light source includes:
 a. at least one lamp disposed in said elongated cavity;
 b. a rod of transparent material having a gradient refraction index optically coupled to said lamp.

14. A dental video camera according to claim 2 wherein said dental video camera also includes a remote control transmitter coupled to said adjustably focusing lens and CCD camera system.

15. A dental video camera according to claim 14 wherein said light source is at least one lamp which provide direct illumination.

16. A dental video camera according to claim 14 wherein said light source includes:
 a. at least one lamp disposed in said elongated cavity;
 b. at least one bundle of optical fibers optically coupled to said lamp.

17. A dental video camera according to claim 14 wherein said light source includes:
 a. at least one lamp disposed in said elongated cavity;
 b. a rod of transparent material having a gradient refraction index optically coupled to said lamp.

* * * * *